United States Patent
Chen et al.

(10) Patent No.: US 7,421,294 B2
(45) Date of Patent: Sep. 2, 2008

(54) SYSTEM AND METHOD FOR PREVENTING RECURRENCE OF ATRIAL TACHYARRHYTHMIA

(75) Inventors: Victor T. Chen, Minnetrista, MN (US); Gary T. Seim, Minneapolis, MN (US); Milton M. Morris, Minneapolis, MN (US)

(73) Assignee: Cardiac Pacemakers, Inc., St. Paul, MO (US)

( * ) Notice: Subject to any disclaimer, the term of this patent is extended or adjusted under 35 U.S.C. 154(b) by 425 days.

(21) Appl. No.: 10/975,553

(22) Filed: Oct. 28, 2004

(65) Prior Publication Data

US 2005/0060000 A1    Mar. 17, 2005

Related U.S. Application Data

(62) Division of application No. 09/662,091, filed on Sep. 14, 2000, now Pat. No. 6,829,504.

(51) Int. Cl.
*A61N 1/362* (2006.01)
(52) U.S. Cl. ...................................... 607/14
(58) Field of Classification Search .................. 607/4, 607/5, 14, 15, 28
See application file for complete search history.

(56) References Cited

U.S. PATENT DOCUMENTS

| | | | |
|---|---|---|---|
| 4,030,510 A | 6/1977 | Bowers | 128/419 PG |
| 4,163,451 A | 8/1979 | Lesnick et al. | 128/419 PG |
| 4,819,643 A | 4/1989 | Menken | 128/419 P |
| 4,830,006 A | 5/1989 | Haluska et al. | 607/4 |
| 4,945,509 A | 7/1990 | Barrett et al. | 128/419 PG |
| 4,998,974 A | 3/1991 | Aker | 128/419 PG |
| 5,042,480 A | 8/1991 | Hedin et al. | 128/419 PG |
| 5,174,289 A | 12/1992 | Cohen | 128/419 |
| 5,207,219 A | 5/1993 | Adams et al. | 128/419 D |

(Continued)

FOREIGN PATENT DOCUMENTS

EP          0033418          8/1981

(Continued)

OTHER PUBLICATIONS

*Metrix Model 3020 Implantable Atrial Defibrillator*, Physician's Manual, InControl, Inc., Redmond, Wa,(1998),pp. 4-24-4-27.

(Continued)

*Primary Examiner*—George R Evanisko
(74) *Attorney, Agent, or Firm*—Schwegman, Lundberg & Woessner, P.A.

(57) ABSTRACT

A system and method for providing pacing pulses after a cardioversion/defibrillation shock, where the pacing pulses have a pacing rate at an initial value. The pacing rate is decreased from the initial value until at least one intrinsic cardiac contraction is detected. In one embodiment, the pacing rate is decreased by a set amount after pacing a set number of cardiac cycles. Providing the set number of pacing pulses and decreasing the pacing rate by the set amount is then repeated until at least one intrinsic cardiac contraction is detected. An intrinsic cardiac rate is then determined from the at least one intrinsic cardiac contraction. The pacing rate is then increased and maintained to be above (i.e., greater than) the intrinsic cardiac rate.

11 Claims, 6 Drawing Sheets

U.S. PATENT DOCUMENTS

| | | | |
|---|---|---|---|
| 5,265,600 A | 11/1993 | Adams et al. | 607/4 |
| 5,267,560 A | 12/1993 | Cohen | 607/25 |
| 5,269,299 A | 12/1993 | Duncan | 128/419 PG |
| 5,282,836 A | 2/1994 | Kreyenhagen et al. | 607/4 |
| 5,284,491 A | 2/1994 | Sutton et al. | 607/17 |
| 5,292,339 A | 3/1994 | Stephens et al. | 607/15 |
| 5,301,669 A | 4/1994 | Duncan | 607/9 |
| 5,334,220 A | 8/1994 | Sholder | 607/9 |
| 5,342,405 A | 8/1994 | Duncan | 607/17 |
| 5,350,409 A | 9/1994 | Stoop et al. | 607/17 |
| 5,356,425 A | 10/1994 | Bardy et al. | 607/14 |
| 5,395,397 A | 3/1995 | Lindgren et al. | 607/9 |
| 5,411,524 A | 5/1995 | Rahul | 607/4 |
| 5,458,623 A | 10/1995 | Lu et al. | 607/28 |
| 5,462,060 A | 10/1995 | Jacobson et al. | 128/702 |
| 5,480,413 A | 1/1996 | Greenhut et al. | 607/14 |
| 5,507,784 A | 4/1996 | Hill et al. | 607/14 |
| 5,522,859 A | 6/1996 | Stroebel et al. | 607/19 |
| 5,534,016 A | 7/1996 | Boute | 607/9 |
| 5,584,864 A | 12/1996 | White | 607/5 |
| 5,591,215 A | 1/1997 | Greenhut et al. | 607/14 |
| 5,601,613 A | 2/1997 | Florio et al. | 607/14 |
| 5,626,620 A | 5/1997 | Kieval et al. | 607/9 |
| 5,676,687 A * | 10/1997 | Ayers | 607/4 |
| 5,713,929 A | 2/1998 | Hess et al. | 607/14 |
| 5,725,561 A | 3/1998 | Stroebel et al. | 607/9 |
| 5,788,717 A | 8/1998 | Mann et al. | 607/14 |
| 5,792,193 A | 8/1998 | Stoop | 607/14 |
| 5,814,077 A | 9/1998 | Sholder et al. | 607/9 |
| 5,814,085 A | 9/1998 | Hill | 607/14 |
| 5,840,079 A | 11/1998 | Warman et al. | 607/4 |
| 5,846,263 A | 12/1998 | Peterson et al. | 607/14 |
| 5,865,838 A | 2/1999 | Obel et al. | 607/5 |
| 5,873,895 A | 2/1999 | Sholder et al. | 607/9 |
| 5,928,271 A | 7/1999 | Hess et al. | 607/14 |
| 5,954,752 A | 9/1999 | Mongeon et al. | 607/6 |
| 5,968,081 A | 10/1999 | Levine | 607/9 |
| 5,978,709 A | 11/1999 | Begemann et al. | 607/14 |
| 5,983,138 A | 11/1999 | Kramer | 607/9 |
| 5,999,850 A | 12/1999 | Dawson et al. | 607/14 |
| 6,047,210 A | 4/2000 | Kim et al. | 607/4 |
| 6,058,328 A | 5/2000 | Levine et al. | 607/14 |
| 6,067,473 A | 5/2000 | Greeninger et al. | 607/32 |
| 6,081,746 A | 6/2000 | Pendekanti et al. | 607/5 |
| 6,081,747 A | 6/2000 | Levine et al. | 607/9 |
| RE36,765 E | 7/2000 | Mehra | 607/4 |
| 6,141,586 A | 10/2000 | Mower | 607/9 |
| 6,285,907 B1 | 9/2001 | Kramer et al. | 607/9 |
| 6,351,669 B1 | 2/2002 | Hartley et al. | 607/5 |
| 6,829,504 B1 * | 12/2004 | Chen et al. | 607/4 |

FOREIGN PATENT DOCUMENTS

| | | |
|---|---|---|
| EP | 0518599 | 12/1992 |

OTHER PUBLICATIONS

"Harmony, Automatic Dual Chamber Pacemaker, Product Information and Programming Guide", Viatron Medical, 22 p., (Date Unknown), Harmony Dual Chamber mentioned in publication Clinica, 467, p. 16, Sep. 11, 1991, "Rate Devices Impact Pacemaker Market", also mentioned in Clinica, 417, p. 9, Sep. 5, 1990 "French CNH Equipment Approvals"., 22 p.

Duckers, H. J., et al., "Effective use of a novel rate-smoothing algorithm in atrial fibrillation by ventricular pacing", *European Heart Journal*, 18, (1997),pp. 1951-1955.

Fahy, G. J., et al., "Pacing Strategies to Prevent Atrial Fibrillation", *Atrial Fibrillation*, 14 (4), (Nov. 1996),pp. 591-596.

Greenhut, S., et al., "Effectiveness of a Ventricular Rate Stabilization Algorithm During Atrial Fibrillation in Dogs", *Pace Abstract*, Abstract No. 60, (1996), 1 p.

Heuer, H., et al., "Dynamic Dual-Chamber Overdrive Pacing with an Implantable Pacemaker System: A New Method for Terminating Slow Ventricular Tachycardia", *Zeitschrift fur Kardiologie*, 75, German Translation by the Ralph McElroy Translation Company, Austin, TX,(1986),5 p.

Mehra, R., et al., "Prevention of Atrial Fibrillation/Flutter by Pacing Techniques", *Interventional Electrophysiology, Second Edition*, Chapter 34, Futura Publishing Company, Inc.,(1996),pp. 521-540.

Skanes, A.C., et al., "Effects of Postshock Atrial Pacing on Atrial Defibrillation Outcome in the Isolated Sheep Heart", *Circulation*, (Jun. 28, 1998),64-72.

Tse, Hung-Fat, et al., "Atrial fibrillation detection and R-wave synchronization by Metrix implantable atrial defibrillator: implications for long-term efficacy and safety. The Metrix Investigators", *Circulation*, 99(11), (Mar. 23, 1999),1446-1451.

Tse, Hung-Fat, et al., "Atrial pacing for suppression of early reinitiation of atrial fibrillation after successful internal cadiovascular", *European Heart Journal*, 21(14), (Jul. 2000), 1167-1176.

Wittkampf, F.H.M., et al., "Rate Stabilization by Right Ventricular Pacing in Patients with Atrial Fibrillation", *Pace*, vol. 9, Part II, (Nov.-Dec. 1986),1147-1153.

"U.S. Appl. No. 09/316,682 Non Final Office action mailed Jan. 19, 2001", 4 pgs.

"U.S. Appl. No. 09/316,682 Notice of allowance mailed May 11, 2001", 3 pgs.

"U.S. Appl. No. 09/316,682 Notice of allowance mailed Aug. 9, 2001", 5 pgs.

"U.S. Appl. No. 09/316,682 Response filed Apr. 12, 2001 to Non Final Office action mailed Jan. 19, 2001", 6 pgs.

* cited by examiner

SYSTEM AND METHOD FOR PREVENTING RECURRENCE OF ATRIAL TACHYARRHYTHMIA

CROSS-REFERENCE TO RELATED APPLICATIONS

This application is a division of application Ser. No. 09/662,091, filed on Sep. 14, 2000, now issued as U.S. Pat. No. 6,829,504, the specification of which is incorporated herein by reference.

TECHNICAL FIELD

This invention relates generally to cardiac rhythm management systems and particularly, but not by way of limitation, to a cardiac rhythm management system and method for preventing recurrence of atrial tachyarrhythmias.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation shock. The shock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management systems is the proper treatment of atrial tachyarrhythmias, such as atrial fibrillation. Atrial fibrillation is a common cardiac arrhythmia which reduces the pumping efficiency of the heart, though not to as great a degree as in ventricular fibrillation. However, this reduced pumping efficiency requires the ventricle to work harder, which is particularly undesirable in sick patients that cannot tolerate additional stresses. As a result of atrial fibrillation, patients must typically limit their activity and exercise.

Although atrial fibrillation, by itself, is usually not life-threatening, prolonged atrial fibrillation may be associated with strokes, which are thought to be caused by blood clots forming in areas of stagnant blood flow. Treating such blood clots requires the use of anticoagulants. Atrial fibrillation may also cause pain, dizziness, and other irritation to the patient. For this reason, atrial fibrillation is typically treated with a low energy defibrillation shock to enable the resumption of normal atrial heart rhythms.

An even more serious problem, however, is the risk that atrial fibrillation may induce irregular ventricular heart rhythms by processes that are yet to be fully understood. Such induced ventricular arrhythmias compromise pumping efficiency even more drastically than atrial arrhythmias and, in some instances, may be life-threatening. Moreover, treating atrial fibrillation by a defibrillation shock may also induce dangerous ventricular arrhythmias. For these and other reasons, there is a need for safe and more effective atrial therapy that prevents the occurrence of atrial tachyarrhythmias, such as atrial fibrillation, thereby avoiding inducing ventricular arrhythmia as the result of the atrial tachyarrhythmia or its treatment.

SUMMARY

The present subject matter provides a system and method to address the aforementioned problems. In one embodiment, the present subject matter provides a post-defibrillation shock therapy or post-cardioversion therapy which may prevent or slow the recurrence of the arrhythmia which necessitated the shock. Pacing pulses are delivered at an elevated rate relative to normal intrinsic rates after delivering a defibrillation or cardioversion shock. The pacing pulses delivered at this rate initiate and control the contraction of the heart at a rate that is at or just above the heart's own intrinsic rate. By controlling and initiating the cardiac contractions the likelihood of the arrhythmia which necessitated the shock returning is reduced.

In one embodiment, the present system provides for post-defibrillation/cardioversion shock pacing pulses to be delivered to the cardiac region having received the shock. The system begins by delivering the pacing pulses at a predetermined time after the defibrillation shock or cardioversion pulse has been delivered. Alternatively, pacing pulses of the present subject matter are delivered after treating the heart with antitachycardia pacing. The pacing pulses are initially delivered at a pacing rate having an initial value. In one embodiment, the initial value is set well above the intrinsic cardiac rate of the patient. This ensures that the pacing rate used by the system will control the rate and the refractory period of the heart. In one embodiment, the pacing rate has an initial value set in the range of 100 to 200 pacing pulses per minute.

The rate of the pacing pulses is decreased from the initial value down to a point where the intrinsic rate of the heart is detected. In one embodiment, the decrease in the pacing rate occurs as a function of delivered pacing pulses. For example, the pacing rate is decreased by a set amount after a set number of cardiac cycles, where the set number of cardiac cycles is a programmable number. In one embodiment, the set number of cardiac cycles paced and the decrease in the pacing rate by the set amount is repeated until at least one intrinsic contraction is detected.

As the pacing rate is being decreased, the system senses for the intrinsic cardiac contraction from the paced chamber. Once the intrinsic contraction is sensed, an intrinsic cardiac rate is determined. In one embodiment, the intrinsic cardiac rate is determined between the paced event and the intrinsic event. Alternatively, the intrinsic cardiac rate is determined between two consecutive intrinsic events (e.g., sensed contractions). The pacing rate is then increased to be above the intrinsic rate, where the pacing rate is then maintained just above the intrinsic rate.

These and other features and advantages of the invention will become apparent from the following description of the preferred embodiments of the invention.

DETAILED DESCRIPTION

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

Providing pacing pulses to a cardiac chamber soon after a defibrillation shock or a cardioversion pulse is delivered may prevent or slow the recurrence of the arrhythmia which necessitated the shock. It has been found that delivering pacing pulses at an elevated rate relative to normal intrinsic rates allows for the rhythm of the heart to be better controlled and the likelihood that an arrhythmia will reoccur lessened. For example, after delivering a defibrillation shock a cardiac chamber is paced at an elevated rate for a period of time, after which the pacing rate is gradually reduced (smoothing the pacing rate) down to the point where the pacing is stopped and the heart's intrinsic rhythm is allowed to resume control. By providing pacing pulses to the cardiac chamber, not only can the contraction rate of the heart be controlled, but the refractory periods of the chamber can be regularized. Regularizing the refractory periods of the cardiac chamber is important in maintaining sinus rhythm (i.e., normal rhythm) of the heart. Once the pacing is stopped, and the heart's own intrinsic rhythm takes over, there is an increased opportunity for irregular refractory periods to occur. Irregular refractory periods increase the chances that the arrhythmia, (e.g., fibrillation or tachycardia) will return. Thus, maintaining pacing control over the heart after a defibrillation shock or cardioversion pulse is important in ensuring that the heart maintains sinus rhythm.

One difficulty with maintaining pacing control over the cardiac chamber is balancing the heart's own intrinsic rate with what elevated pacing rate to use in maintaining control. Provide a pacing rate that is too much above the intrinsic rate may not be desirable for both the patient and for the longevity of the implantable device. Therefore, a system which would allow for elevated pacing, post-defibrillation shock or cardioversion pulse, which would smooth to a pacing rate at or just above the heart's own intrinsic rate is needed.

The present subject matter offers such a system. In one embodiment, the present system provides for post-defibrillation/cardioversion shock pacing pulses to be delivered to the cardiac region having received the shock. The pacing pulses are initially delivered at a pacing rate having an initial value. In one embodiment, the initial value is set well above the intrinsic cardiac rate of the patient. This ensures that the pacing rate used by the system will control the rate and the refractory period of the heart.

In one embodiment, the system begins by delivering the pacing pulses at a predetermined time after a defibrillation shock or cardioversion pulse has been delivered. Alternatively, pacing pulses of the present subject matter are delivered after treating the heart with antitachycardia pacing. The rate of the pacing pulses is then decreased from the initial value down to a point where the intrinsic rate of the heart is detected. In one embodiment, the decrease in the pacing rate occurs as a function of delivered pacing pulses, where the pacing rate is decreased by a set amount after a set number of cardiac cycles, where the set number of cardiac cycles is a programmable number.

As the pacing rate is being decreased, the system senses for an intrinsic cardiac contraction from the paced chamber. Once the intrinsic contraction is sensed, an intrinsic cardiac rate is determined. In one embodiment, the intrinsic cardiac rate is determined between the paced event and the intrinsic event. Alternatively, the intrinsic cardiac rate is determined between two consecutive intrinsic events (e.g., at least two sensed intrinsic contractions, such as intrinsic atrial contractions or intrinsic ventricular contractions). The pacing rate is then increased to be above the intrinsic rate, where the pacing rate is then maintained just above the intrinsic rate, as will be more fully described below.

Figure 1:
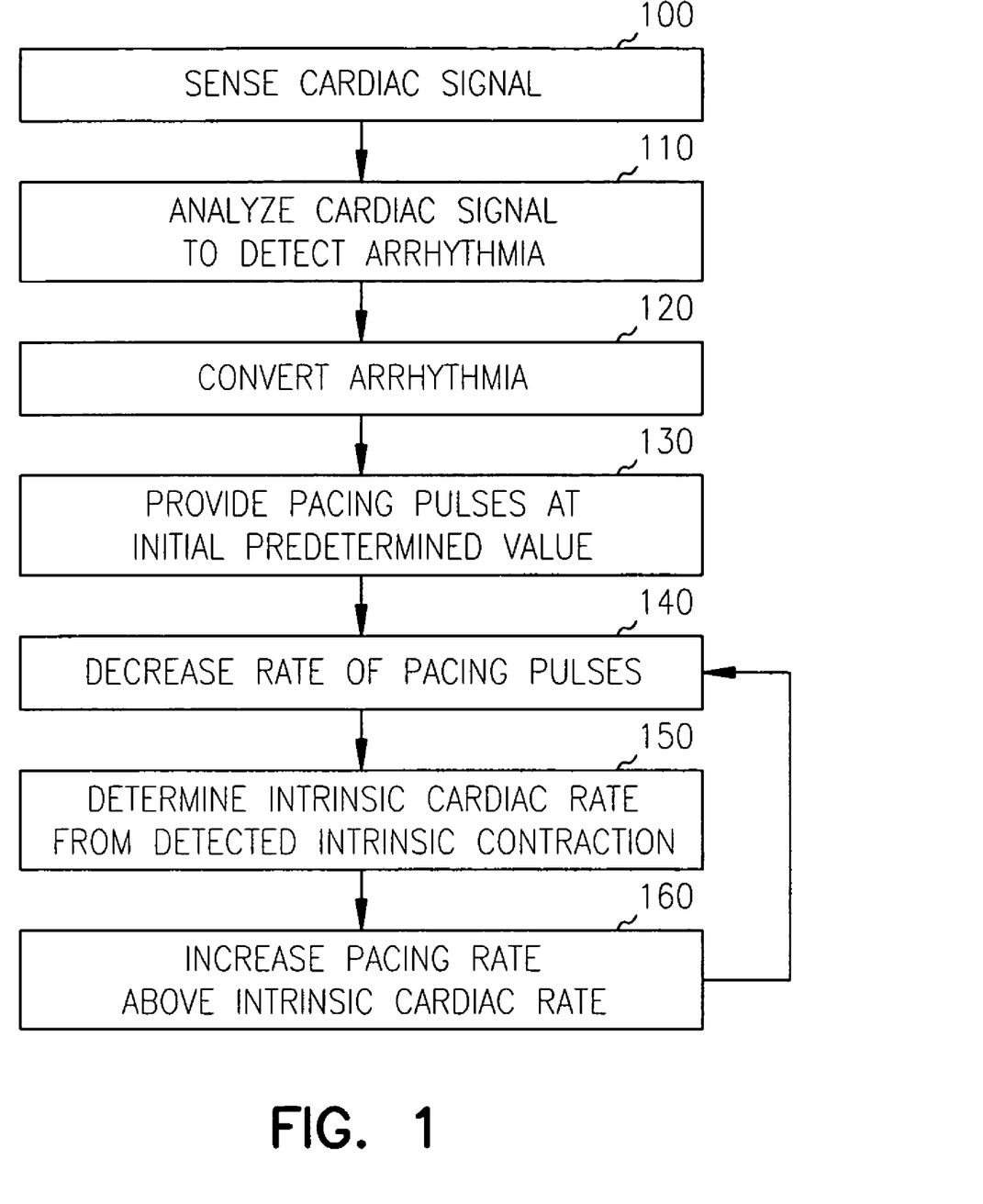
FIG. 1 is a flow chart illustrating one embodiment of the present subject matter.

Referring now to FIG. 1, there is shown one embodiment of a method according to the present subject matter. At 100, an cardiac signal is sensed from one or more cardiac chambers of the heart. In one embodiment, the cardiac signal is either a unipolar signal or a bipolar signal sensed with one or more electrodes implanted within the heart. At 110, the cardiac signal is analyzed to detect an arrhythmia, such as a fibrillation or a tachycardia episode. If an arrhythmia is not detected, the method continues to sense and analyze the cardiac signal. If, however, an arrhythmia is detected, one or more defibrillation shocks, or cardioversion pulses, are used to capture and convert the heart 120. Alternatively, under the appropriate circumstances, antitachycardia pacing is delivered to convert the arrhythmia (e.g., ventricular tachycardia) by stimulating the heart with a rapid series of electrical pulses.

Once captured and converted, pacing pulses having a pacing rate at an initial value are provided to the heart at 130. In one embodiment, the first pacing pulse of the pacing pulses is provided at a delay after the defibrillation or cardioversion shock. In one embodiment, the delay is programmable in the range of 0 milliseconds to 1000 milliseconds. In an additional embodiment, the delay is programmable in the range of 0 milliseconds to 500 milliseconds. These given time ranges for delay, however, are exemplary and other time ranges which exceed 1000 milliseconds are considered within the scope of the present subject matter.

In an additional embodiment, the initial value of the pacing rate is set (programmed) at a value equal to or less than the maximum programmable pacing rate value of the implantable pacemaker in which the present subject matter is implemented. For example, the initial value of the pacing rate is set in the range of 100 to 200 pacing pulses per minute (interval durations of 600 to 300 milliseconds). In one embodiment, setting the initial value of the pacing rate includes either fixing the value of the pacing rate or allowing the pacing rate to be a programmable value. In one embodiment, the initial value of the pacing rate is a programmable value that is set above the intrinsic cardiac rate of the patient, where the intrinsic cardiac rate of the patient is determined by the patient's physician. Alternatively, the initial value of the pacing rate is preset and is not adjustable.

The initial value of the pacing rate is used in pacing the heart for a set number of cardiac cycles. In one embodiment, the set number of cardiac cycles is a programmable value in the range of two (2) to one-hundred twenty eight (128) cardiac cycles. Once the heart has been paced at the pacing rate initial value for the set number of cardiac cycles, the pacing rate is then decreased at 140. In one embodiment, the pacing rate is decreased by a set amount for every subsequent set of the number of cardiac cycles until an intrinsic cardiac contraction is detected. Thus, providing the set number of pacing pulses and then decreasing the pacing rate by the set amount is repeated until an intrinsic cardiac contraction is detected. In other words, the pacing rate for each of the set number of cardiac cycles becomes slower and slower, until an intrinsic cardiac contraction is detected.

The pacing rate is then decreased by adding a set value to the interval duration between the pacing pulses. In one embodiment, the set value is in the range of seven and one-half (7.5) milliseconds to ten (10) milliseconds. Thus, for an initial pacing rate of 200 pacing pulses per minute and a set value of 10 milliseconds, after the first decrease the pacing rate would be approximately 193.5 pacing pulses per minute, after the second decrease the pacing rate would be approximately 187.5 pacing pulses per minute, and so forth until an intrinsic cardiac contraction is detected. In an alternative embodiment, the set value includes additional values which allow for changes to the pacing rate according to the present subject matter (e.g., set values less than 7.5 milliseconds and set values greater than 10 milliseconds).

At 150, once the intrinsic contraction is detected, an intrinsic cardiac rate is determined. In one embodiment, the intrinsic cardiac rate is the rate determined from the time interval between the paced cardiac event and the subsequent intrinsic cardiac event. In an alternative embodiment, the intrinsic rate is determined from two consecutive sensed intrinsic cardiac contractions. Once the intrinsic cardiac rate is determined at 150, the pacing rate is increased at 160 to be greater than the intrinsic cardiac rate. In one embodiment, the pacing rate is increased by subtracting the value to the interval duration between the pacing pulses. Thus, once the intrinsic rate is determined the cardiac pacing rate is increased by the margin of the value so the pacing pulses control the contraction of the heart, and not the intrinsic mechanisms of the heart (i.e., the SA-node). The increased pacing rate is then used in delivering the pacing pulse after the intrinsic pulse is detected.

The system then returns to 140, where the pacing rate is allowed decrease as previously described until the next intrinsic contraction is detected. The system then proceeds to 150, where the intrinsic rate is determined as previously described. The system then proceed through 160 and back to 140. This allows the heart to be paced at, or nearly at, the intrinsic rate, while still being under the control of a pulse generator. Thus, the pacing rate is maintained at or above the intrinsic cardiac rate. As previously discussed, this allows the refractory period of the cardiac chamber to be controlled so as to reduce the likelihood of recurrence of the arrhythmia or tachyarrhythmia.

The post-shock therapy of the present subject matter is then discontinued after a predetermined time interval. In one embodiment, the predetermined time interval is a programmable or a set value of up to 15 minutes. After the predetermined time interval expires, the system resumes any previously suspended pacing protocols and returns to sense the cardiac signal from one or more cardiac chambers of the heart at 100. Alternatively, the post-shock therapy according to the present subject matter is discontinued and the system returns to 100 after a predetermined number of intrinsic pulses are detected. In one embodiment, the predetermined number of intrinsic pulses is programmed or set in the range of 0 to 15 sensed intrinsic pulses.

Figure 2:
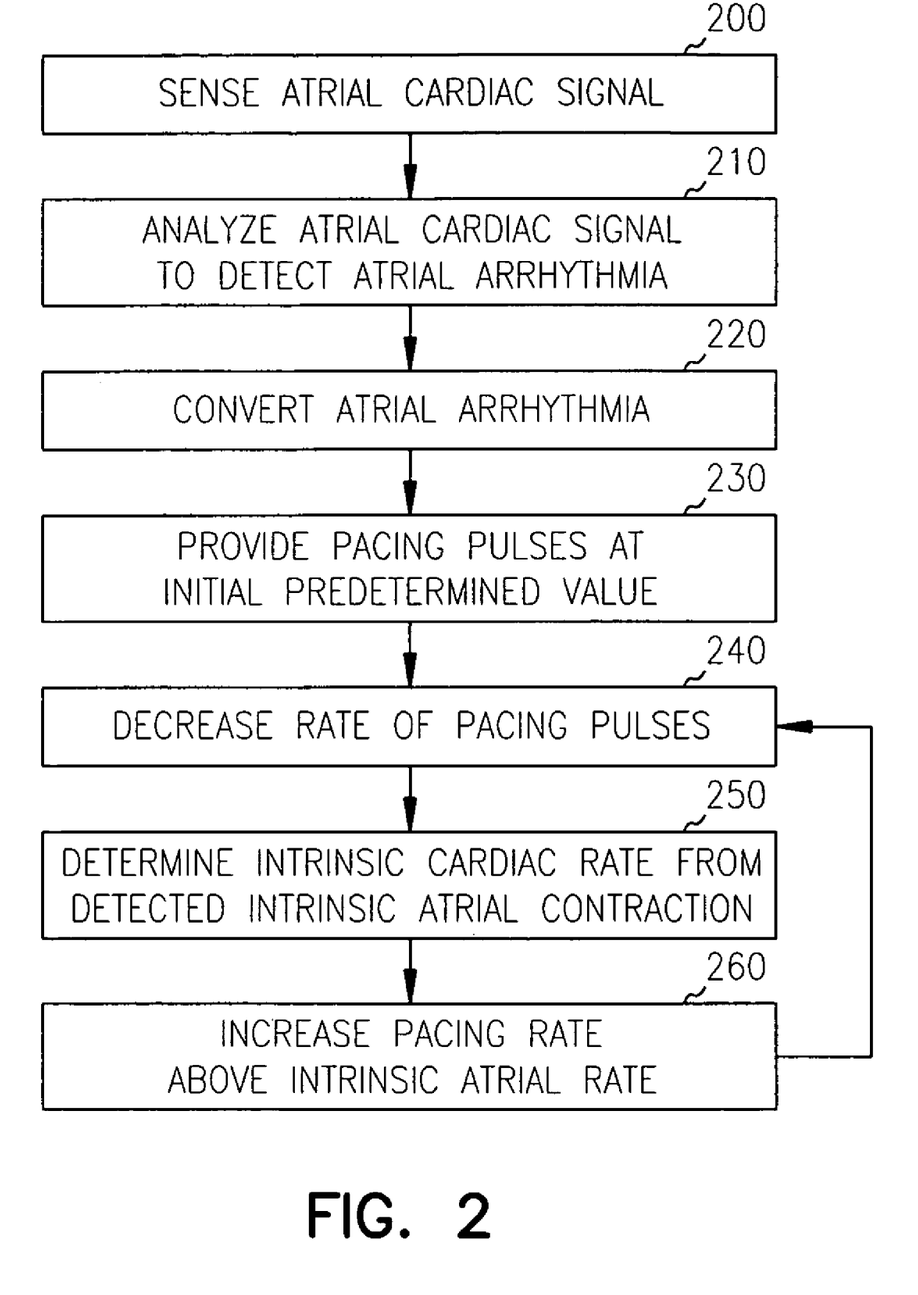
FIG. 2 is a flow chart illustrating one embodiment of the present subject matter.

Referring now to FIG. 2, there is shown an additional embodiment of a method according to the present subject matter. The embodiment of FIG. 2 is specific to atrial arrhythmias and where pacing pulses are delivered to the atrium. It will be appreciated that the present subject matter can be applied to other cardiac regions, including, but not limited to, ventricular chambers of the heart (e.g., right and/or left ventricles) and/or atrial chambers of the heart (e.g., right and/or left atria).

At 200, an atrial signal is sensed from the atrium. In one embodiment, the atrial signal is either a unipolar signal or a bipolar signal sensed with one or more electrodes implanted within the heart. At 210, the atrial signal is analyzed to detect an atrial fibrillation or atrial tachycardia. In one embodiment, the atrial rate is used as a criteria for determining the presence of an atrial fibrillation and/or atrial tachycardia. Other techniques of determining the occurrence of atrial fibrillation and/or atrial tachycardia are possible. If an atrial fibrillation or tachycardia are not detected, the method continues to sense and analyze the atrial signal. If an atrial fibrillation or tachycardia is detected, one or more atrial defibrillation shocks, or atrial cardioversion pulses, are used to capture and convert the atrial chambers at 220.

Once captured and converted, pacing pulses having a pacing rate at an initial value are provided to the atrium at 230. In one embodiment, a first pacing pulse of the pacing pulses is provided at a delay after the defibrillation or cardioversion shock. In one embodiment, the delay is programmable in the range of 0 milliseconds to 1000 milliseconds. In an additional embodiment, the delay is programmable in the range of 0 milliseconds to 500 milliseconds. These given time ranges for delay, however, are exemplary and other time ranges which exceed 1000 milliseconds are considered within the scope of the present subject matter.

In an additional embodiment, the initial value of the pacing rate is set (programmed) at a value equal to or less than the maximum programmable pacing rate value of the implantable pacemaker in which the present subject matter is implemented. For example, the initial value of the pacing rate is set in the range of 100 to 200 pacing pulses per minute (interval durations of 600 to 300 milliseconds). In one embodiment, setting the initial value of the pacing rate includes either fixing the value of the pacing rate or allowing the pacing rate to be a programmable value. In one embodiment, the initial value of the pacing rate is a programmable value that is set above the intrinsic cardiac rate of the patient, where the intrinsic cardiac rate of the patient is determined by the patient's physician. Alternatively, the initial value of the pacing rate is preset and is not adjustable.

The initial value of the pacing rate is used in pacing the atrium for a set number of cardiac cycles. In one embodiment, the number of cardiac cycles is a programmable value in the range of two (2) to one-hundred twenty eight (128) cardiac cycles. Once the atrium has been paced at the pacing rate initial value for the set number of cardiac cycles, the pacing rate is then decreased at 240. In one embodiment, the pacing rate is decreased by a set amount for every subsequent set of the set number of cardiac cycles until an intrinsic atrial contraction is detected. Thus, providing the set number of pacing pulses and then decreasing the pacing rate by the set amount is repeated until an intrinsic atrial contraction is detected. In other words, the pacing rate for each group of the set number of cardiac cycles becomes slower and slower, until an intrinsic atrial contraction is detected. In one embodiment, the pacing rate is decreased by adding the value to the interval duration between the pacing pulses, where the value is in the range of seven and one-half (7.5) milliseconds to ten (10) milliseconds. Thus, for an initial pacing rate of 200 pacing pulses per minute and a set value of 10 milliseconds, after the first decrease the pacing rate would be approximately 193.5 pacing pulses per minute, after the second decrease the pacing rate would be approximately 187.5 pacing pulses per minute, and so forth until an intrinsic cardiac contraction is detected. In an alternative embodiment, the set value includes additional values which allow for changes to the pacing rate according to the present subject matter (e.g., set values less than 7.5 milliseconds and set values greater than 10 milliseconds).

At 250, once the intrinsic contraction is detected, an intrinsic atrial rate is determined. In one embodiment, the intrinsic atrial rate is the rate determined from the time interval between paced atrial event and the subsequent intrinsic atrial event. In an alternative embodiment, the intrinsic rate is determined from two consecutive sensed intrinsic atrial contractions. Once the intrinsic atrial rate is determined at 250, the pacing rate is increased at 260 to be greater than the intrinsic atrial rate. In one embodiment, the pacing rate is increased by subtracting the value to the interval duration between the pacing pulses. Thus, once the intrinsic rate is determined the atrial pacing rate is increased by the margin of the value so the pacing pulses control the contraction of the atrium, and not the intrinsic mechanisms of the heart (i.e., the SA-node). The increased pacing rate is then used in delivering the pacing pulse after the intrinsic pulse is detected.

The system then returns to 240, where the pacing rate is allowed decrease as previously described until the next intrinsic contraction is detected. The system then proceeds to 250, where the intrinsic rate is determined as previously described. The system then proceed through 260 and back to 240. This allows the atrium to be paced at, or nearly at, the intrinsic rate of the atrium, while still being under the control of the pulse generator. Thus, the pacing rate of the atrium is maintained at or above the intrinsic rate of the atrium. As previously discussed, this allows the refractory period of the cardiac chamber to be controlled so as to reduce the likelihood of recurrence of the arrhythmia or tachyarrhythmia.

The post-shock therapy of the present subject matter is then discontinued after a predetermined time interval. In one embodiment, the predetermined time interval is a programmable or a set value of up to 15 minutes. After the predetermined time interval expires, the system resumes any previously suspended pacing protocols and returns to sense the cardiac signal from one or more cardiac chambers of the heart at 200. Alternatively, the post-shock therapy according to the present subject matter is discontinued and the system returns to 200 after a predetermined number of intrinsic pulses are detected. In one embodiment, the predetermined number of intrinsic pulses is programmed or set in the range of 0 to 15 sensed intrinsic pulses.

Figure 3:
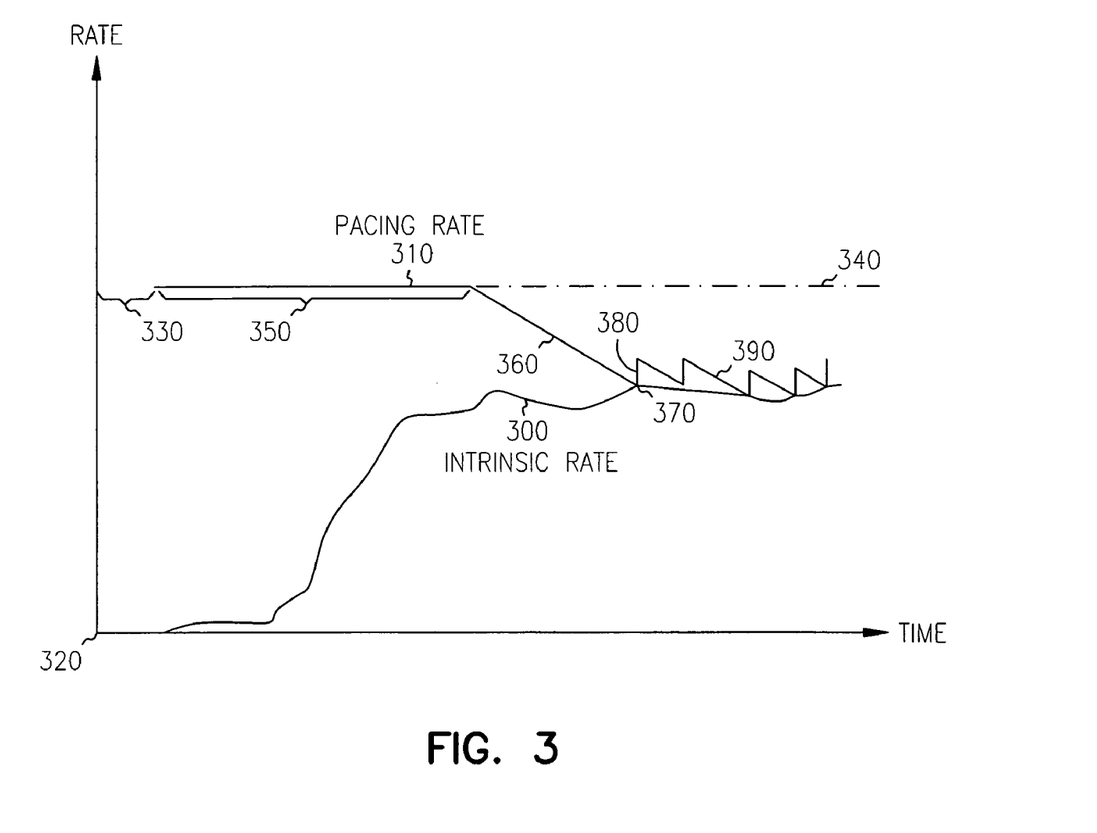
FIG. 3 is a graph of illustrating one embodiment of the present subject matter.

Referring now to FIG. 3, there is shown an example of a post-therapy pacing response according to the present subject matter. FIG. 3 shows a plot of an intrinsic cardiac rate 300 and a pacing rate 310 which are plotted on a rate (beats/time) versus time plot. At 320 a defibrillation or cardioversion shock has been delivered to the heart. No intrinsic cardiac rate is present at this time as the heart is in its refractory period following the shock. Pacing pulses are delivered to the heart after the delay 330, where the pacing pulses are delivered at the initial value 340.

After the set number of paced cardiac cycles 350, the pacing rate is decreased along 360, as previously described. The pacing rate is decreased along 360 as previously described until an intrinsic atrial contraction is detected at 370. Once the intrinsic atrial rate is determined, the pacing rate is then increased at 380 and the pacing rate is maintained at or above the intrinsic rate at 390, as previously described.

In one embodiment, the system of the present subject matter can have a programmable time interval over which the system will operate before the heart is allowed to revert to an intrinsic cardiac rhythm. In one embodiment, the programmable time interval is set in the range of 15 seconds to 1 hour. After this interval, the system would then revert back to any original settings for atrial pacing that might have been programmed into the device.

Figure 4:
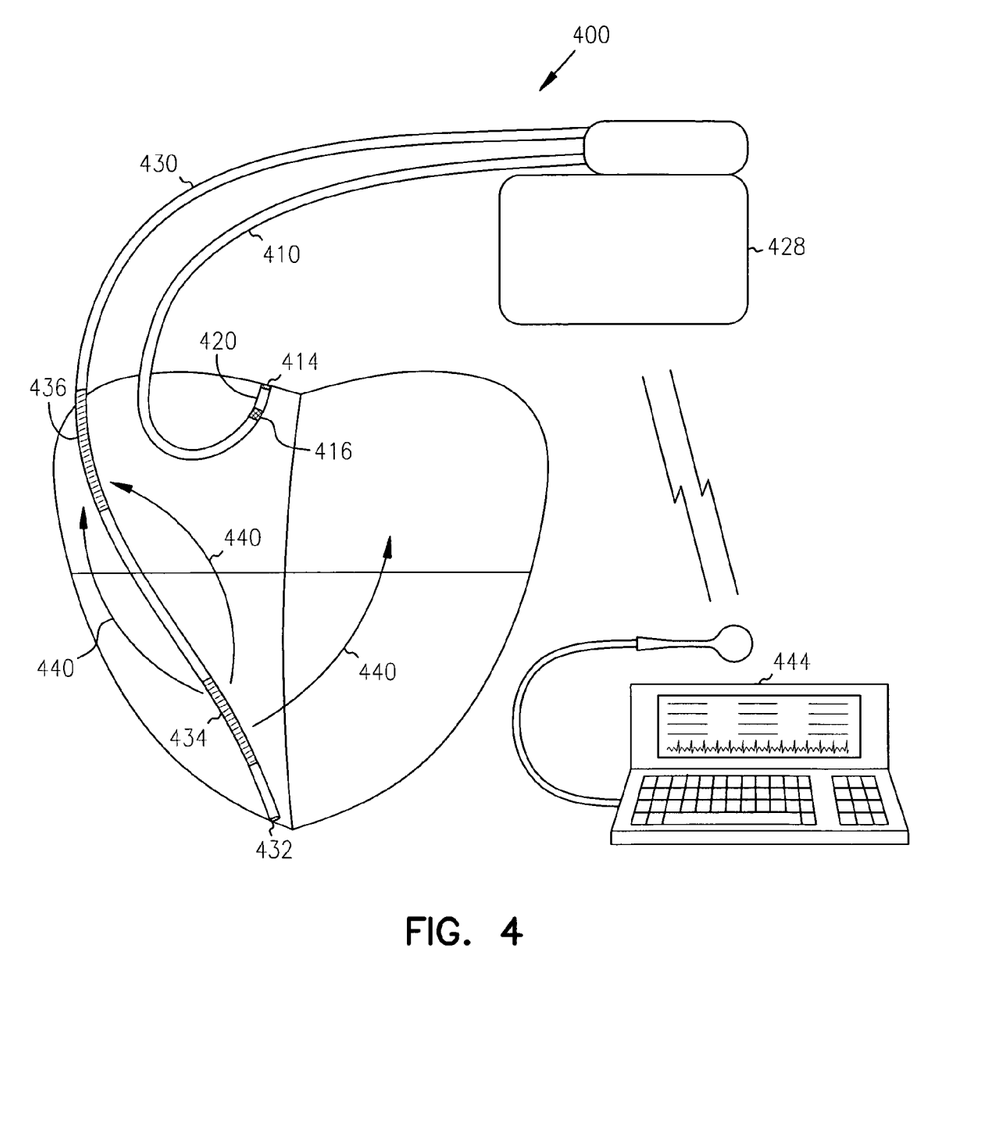
FIG. 4 is a schematic view of one embodiment of an implantable medical device according to one embodiment of the present subject matter.

Referring now to FIG. 4, there is shown one embodiment of a cardiac rhythm management system 400 according to the present subject matter. In the present embodiment, the cardiac rhythm management system 400 includes a first cardiac lead 410 having a first electrode 414 and a second electrode 416. In one embodiment, the first electrode 414 is a pace/sense electrode located at or near a distal end 420 of the first cardiac lead 410. The second electrode 416 is also a pace/sense electrode located proximal the first electrode 414. In one embodiment, the second electrode 416 is a ring electrode which partially or completely encircles the first cardiac lead 410.

In one embodiment, the first electrode 414 is used to sense either a unipolar cardiac signal between the first electrode 414 and the housing 428 of the cardiac rhythm management system 400. Alternatively, the first electrode 414 and the second electrode 416 are used to sense a bipolar cardiac signal. In the present embodiment, the first cardiac lead 410 is a J-tip lead, where the first electrode 414 is located at the distal tip of the lead 410.

The cardiac rhythm management system 400 further includes a second cardiac lead 430. In one embodiment, the second cardiac lead 430 includes a first pace/sense electrode 432, a first defibrillation electrode 434 and a second defibrillation electrode 436. The second cardiac lead 430 is implanted with the distal end of the lead implanted in the right ventricle of the heart, with the first defibrillation electrode 434 located in the right ventricular chamber and the second defibrillation electrode 436 located in the right atrium and/or major vein leading to the right atrium (e.g., superior vena cava). With the second lead 430, ventricular cardiac signals can be sensed between the electrodes. For example, a rate signal (near field signal) is sensed between either the first pace/sense electrode 432 and the first defibrillation electrode 434, or between the first pace/sense electrode 432 and the housing 428. A far field signal can also be sensed between the first and second defibrillation electrodes 434 and 436. In one embodiment, defibrillation and cardioversion pulses are delivered between the first defibrillation electrode 434, and the second defibrillation electrode 436 and the housing 428, as shown by arrows 440. The defibrillation and cardioversion pulses are delivered, in the present example, in response to an atrial arrhythmia as previously described. Alternatively, the defibrillation and/or cardioversion pulses could be delivered in response to a ventricular arrhythmia.

The cardiac rhythm management system 400 includes control circuitry coupled to the first electrode 414 and the second electrode 416 from which a cardiac signal is sensed. The first electrode 414 and the second electrode 416 are shown implanted in a supraventricular region (i.e., atrial region) of the heart, from which an atrial cardiac signal can be sensed and to which pacing pulses can be delivered according the present subject matter. In one embodiment, pacing pulses can be delivered between either the first electrode 414 and the housing 428 or the first electrode 414 and the second electrode 416. In addition, atrial defibrillation shocks and/or cardioversion pulses can be delivered by the control circuitry between the first defibrillation electrode 434, and the second defibrillation electrode 436 and the housing 428, as shown by arrows 440.

FIG. 4 also shows a medical device programmer 444. The medical device programmer 444 and the cardiac rhythm management system 400 include communication circuitry which allows for cardiac data to be to and from the cardiac rhythm management system 400. In addition, command signals for controlling the operation of the cardiac rhythm management system 400 can also be sent between the medical device programmer 444 and the cardiac rhythm management system 400. In one embodiment, communication between the medical device programmer 444 and the cardiac rhythm management system 400 is established over a radio frequency telemetry channel.

Figure 5:
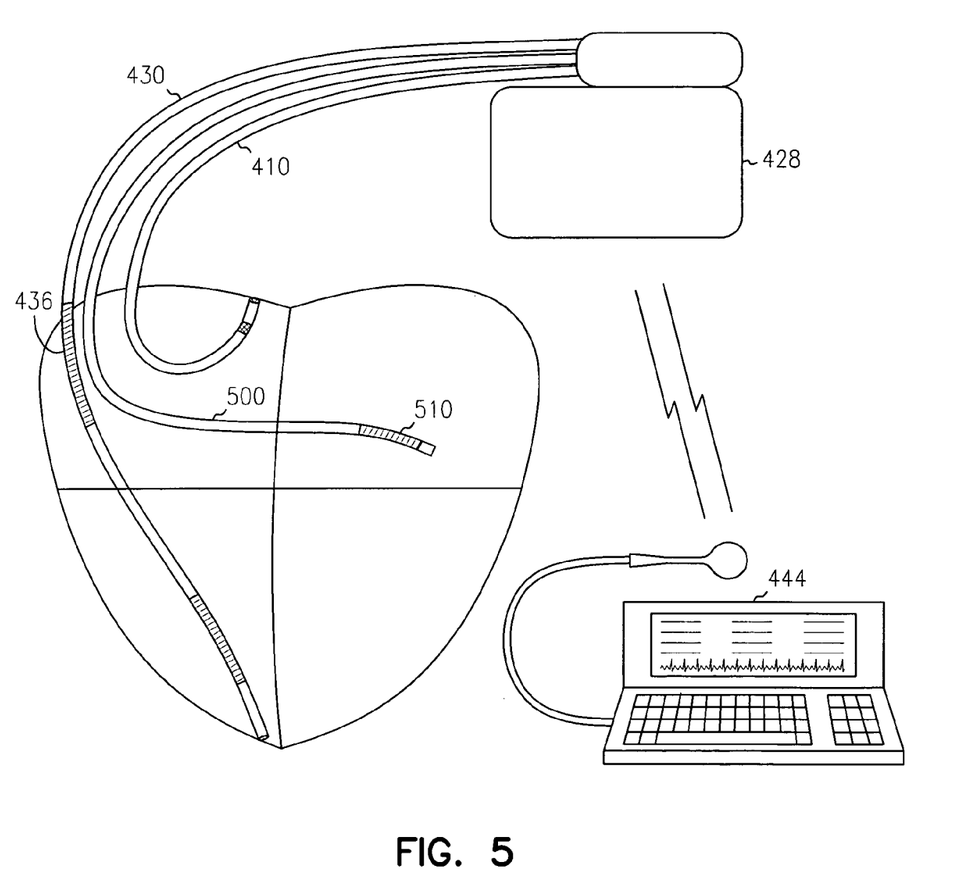
FIG. 5 is a schematic view of one embodiment of an implantable medical device according to one embodiment of the present subject matter.

Referring to FIG. 5, there is shown an additional embodiment of the system shown in FIG. 4, where in addition to a first and second cardiac lead 410 and 430, there is shown a third cardiac lead 500 having at least one defibrillation electrode 510. In one embodiment, the third cardiac lead 500 is positioned in a supraventricular location with at least one defibrillation electrode 510 positioned within the coronary sinus and/or great cardiac vein. With the addition of the third cardiac lead 500, cardioversion and/or defibrillation pulses can be delivered between any number of the defibrillation electrodes. For example, cardioversion/defibrillation pulses can be delivered between defibrillation electrode 510 and the second defibrillation electrode 436 and the housing 428. Other shocking patterns are also possible and considered within the scope of the present subject matter.

Figure 6:
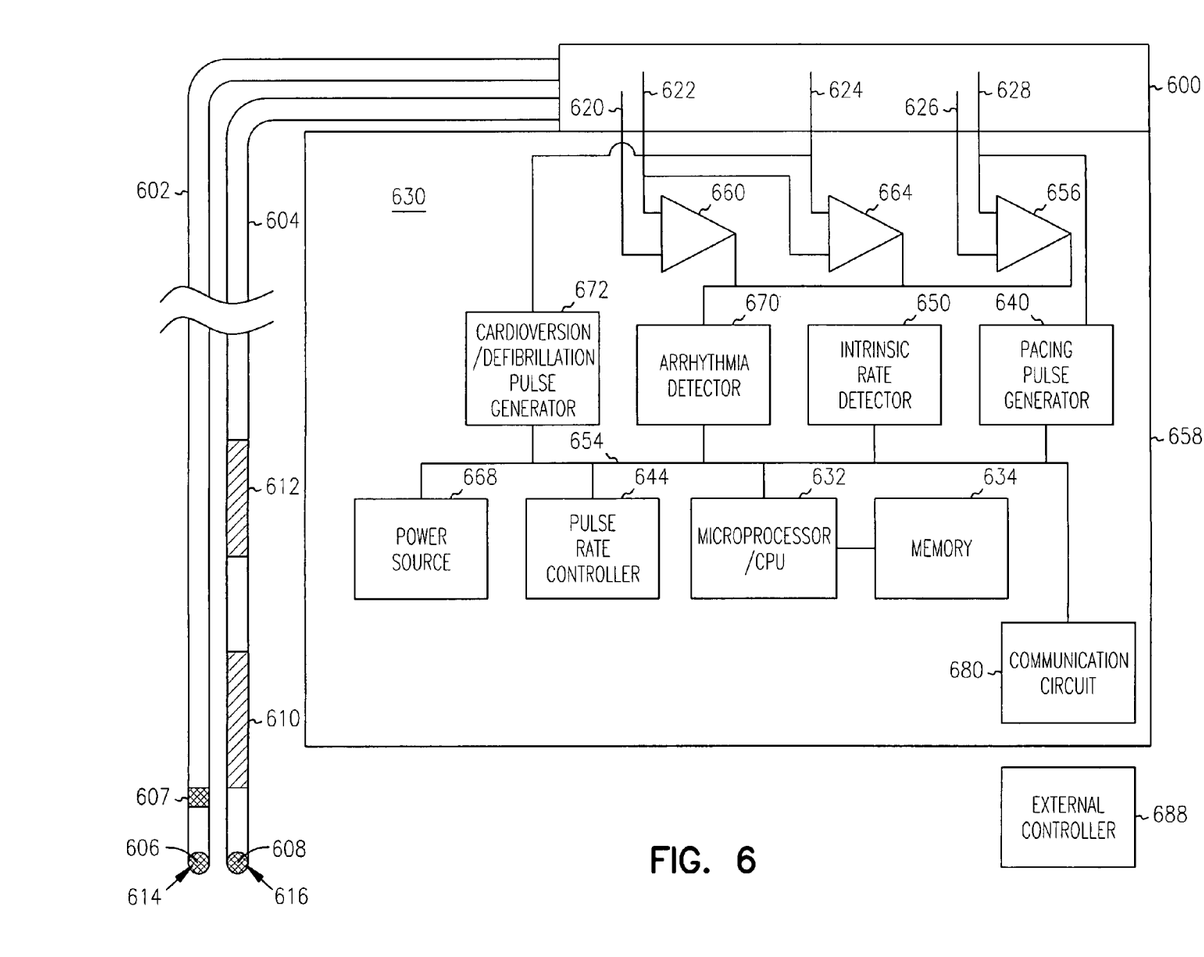
FIG. 6 is a block diagram of one embodiment of an implantable medical device according to the present subject matter.

Referring now to FIG. 6, there is shown one embodiment of a cardiac rhythm management system according to the present subject matter. The system includes an implantable cardiac rhythm management device 600, a first cardiac lead 602 and a second cardiac lead 604 (not to scale). In the embodiment shown in FIG. 6, the first cardiac lead 602 is shown with a first electrode 606 and a second electrode 607, and the second cardiac lead 604 is shown with a first electrode 608, a first defibrillation electrode 610 and a second defibrillation electrode 612. In one embodiment, the first electrode 606 and the second electrode 607 are pace/sense electrodes, where the first electrode 606 is a porous tip electrode positioned at a distal end 614 of the first cardiac lead 602 and the second electrode 607 is a ring electrode either partially or completely encircling the first cardiac lead 602 and is positioned proximal to the first electrode 606. The first electrode 608 is also a pace/sense electrode positioned at the distal end 616 of the second cardiac lead 604.

In one embodiment, the first electrode 606 and the second electrode 607 of the first cardiac lead 602 are implanted within the supraventricular region of the heart as previously described. The second cardiac lead 604 is implanted within the heart, where the distal end of the lead 604 is implanted at the apex of the right ventricle to allow the first electrode 608 and the first defibrillation electrode 610 to be within the right ventricular chamber of the heart and the second defibrillation electrode 612 in the supraventricular region of the heart. In one embodiment, the first electrode 608 and the first defibrillation electrode 610 are used to detect a near field signal (a rate signal) and the first defibrillation electrode 610 and the second defibrillation electrode 612 are used to detect a far field signal (a morphology signal) from the heart.

The electrodes are connected to electronic circuitry within the implantable cardiac rhythm management device 600 through lead conductors housed and electrically insulated within the body of the first and second cardiac leads 602 and 604. The lead conductors are coupled to lead connectors on the cardiac leads, which allow for the electrodes positioned on the leads to be coupled to the electronic circuitry through input terminals 620, 622, 624, 626 and 628. In one embodiment, the first and second cardiac leads 602 and 604 have elongated bodies made of one or more materials suitable for implantation in a human body, where such materials are known. Additionally, the electrodes are constructed of electrically conductive materials, such as platinum, platinum-iridium alloys, or other alloys as are known. The lead conductors are also constructed of electrically conductive materials such as MP35N, an alloy of nickel, chromium, cobalt, and molybdenum.

The implantable cardiac rhythm management device 600 includes control circuitry 630, where the control circuitry 630 is coupled to the electrodes 606, 607, 608, 610 and 612, from which at least a first cardiac signal is sensed, electrical energy pulses are generated under predetermined conditions, and providing electrical energy to electrodes positioned on the leads under the predetermined conditions. In one embodiment, the control circuitry 630 is a programmable microprocessor-based system, with a microprocessor 632 and a memory circuit 634, which contains parameters for various pacing and sensing modes and stores data indicative of cardiac signals received by the control circuitry 630. The control circuitry 630 is shown having various modules, which are implemented either in hardware or as one or more sequences of steps carried out on the microprocessor or other microcontroller. It is understood that the various modules of control circuitry 630 need not be separately embodied, but may be combined or otherwise implemented differently, such as in software/firmware.

The control circuitry 630 includes a pacing pulse generator 640, a pulse rate controller 644, and an intrinsic rate detector 650 which are coupled through bus 654. In one embodiment, the pacing pulse generator 640 produces pacing pulses to be delivered through at least the first electrode, where the pacing pulse generator 640 is controlled by the pulse rate controller 644 to generate pacing pulses at the pacing rate, as previously described.

The implantable cardiac rhythm management device 600 further includes a first sensor 656 coupled to input terminals 626 and 628 to allow for a bipolar cardiac signal to be sensed through the first and second electrodes 606 and 607. Alternatively, a unipolar cardiac signal could be sensed between the first electrode 606 and the housing 658 of the implantable cardiac rhythm management device 600. In addition to the first sensor 656, the implantable cardiac rhythm management device 600 further includes a second sensor 660 and a third sensor 664. In one embodiment, first and second defibrillation electrodes 610 and 612 are coupled to second sensor 660 to allow for a bipolar morphology signal to be sensed between the electrodes. In addition, first electrode 608 and first defibrillation electrode 610 are coupled to the third sensor 664 to allow for a bipolar rate signal to be sensed between the electrodes. The pacing pulse generator 640 is coupled to at least the first electrode 606 and produces electrical pulses to be delivered to the first electrode 606, as previously described. Power to the implantable cardiac rhythm management device 600 is supplied by an electrochemical battery 668 that is housed within the device 600.

The output of each of the sensors 656, 660 and 664 is received by an arrhythmia detector 670. In one embodiment, the arrhythmia detector 670 analyzes the sensed cardiac signals for the occurrence of sensed cardiac contractions and the presence of arrhythmias. In one embodiment, the arrhythmia detector 670 analyze the cardiac signal being detected from the atrial region for the occurrence of an atrial arrhythmia. When an atrial arrhythmia is detected, one or more pulses of cardioversion and/or defibrillation energy are generated by the cardioversion/defibrillation pulse generator 672. The energy can then be delivered to the atrial region through combinations of the first defibrillation electrode 610, second defibrillation electrode 612 and housing 658 to convert the atrial arrhythmia, as previously described. Alternatively, the pacing pulse generator 640 generates antitachycardia pacing for delivery to the atria to convert the atrial arrhythmia, as previously described.

Once the atrial arrhythmia is converted, the pulse rate controller 644 controls the pacing pulse generator 640 to generate pacing pulses at a pacing rate having the initial value, as previously described. In one embodiment, the pulse rate controller 644 controls the pacing pulse generator 640 to provide the first pacing pulse of the pacing pulses at the delay after the electrical pulse, as previously described. The pulse rate controller, through the pacing pulse generator 640, provides pacing pulses to generate the set number of cardiac cycles and then decreases the pacing rate by the set amount, as previously discussed, until an intrinsic contraction is detected in the cardiac signal. The intrinsic contraction is detected by the intrinsic rate detector 650, where the intrinsic rate detector 650 also determines the intrinsic rate with the detected intrinsic contraction, as previously described. Once the intrinsic rate is determined, the pulse rate controller 644 then increases and maintains the pacing rate of the pacing pulses above the intrinsic rate, as previously described.

Electronic communication circuitry 680 is additionally coupled to the control circuitry 630 to allow communication with an external controller 688. In one embodiment, the electronic communication circuitry 680 includes a data receiver and a data transmitter to send and receive and transmit signals and cardiac data to and from an external programmer 688. In one embodiment, the data receiver and the data transmitter include a wire loop antenna to establish a radio frequency telemetric link, as is known in the art, to receive and transmit signals and data to and from the programmer unit 688.

This application is intended to cover any adaptations or variations of the present invention. For example, while atrial arrhythmia has been one focus of the present subject matter, it is recognized that the same concepts and ideas can be applied to the ventricular arrhythmias. Therefore, the foregoing discussion for the present system is not limited to atrial arrhythmias. It is manifestly intended that this invention be limited only by the claims and equivalents thereof.

We claim:

1. A method, comprising:
providing pacing pulses after an atrial defibrillation shock, wherein the pacing pulses have a pacing rate at an initial value that is well above an intrinsic rate;
decreasing the pacing rate from the initial value;
detecting at least one intrinsic atrial contraction after the atrial defibrillation shock;
determining an intrinsic atrial rate from the at least one detected intrinsic atrial contraction; and
increasing the pacing rate above the determined intrinsic atrial rate.

2. The method of claim 1, including setting the initial value of the pacing rate in a range of 100 to 200 pacing pulses per minute.

3. The method of claim 1, wherein decreasing the pacing rate includes pacing a set number of cardiac cycles;
decreasing the pacing rate by a set amount; and
repeating providing the set number of pacing pulses and decreasing the pacing rate by the set amount until at least one intrinsic atrial contraction is detected.

4. The method of claim 1, wherein detecting the at least one intrinsic atrial contraction includes detecting the at least one intrinsic atrial contraction after a pacing pulse of the pacing pulses and determining the intrinsic atrial rate includes determining the intrinsic atrial rate from the pacing pulse and the intrinsic atrial contraction.

5. The method of claim 1, including sensing an atrial signal;
detecting an atrial fibrillation from the sensed atrial signal;
providing an atrial defibrillation shock after detecting the atrial fibrillation; and
providing a first pacing pulse of the pacing pulses at a delay after the atrial defibrillation shock.

6. The method of claim 1, wherein decreasing the pacing rate includes increasing an interval between the pacing pulses by a set value in the range of 7.5 to 10 milliseconds.

7. The method of claim 1, wherein increasing the pacing rate includes maintaining the pacing rate at or above the intrinsic rate.

8. The method of claim 7, wherein maintaining the pacing rate at or above the intrinsic rate includes decreasing an interval between the pacing pulses by a set value in the range of 7.5 to 10 milliseconds.

9. The method of claim 1, wherein determining the intrinsic atrial rate from the at least one intrinsic atrial contraction includes determining the intrinsic atrial rate from at least two intrinsic atrial contractions.

10. A method, comprising:
sensing an atrial cardiac signal;
analyzing the atrial cardiac signal to detect an atrial tachyarrhythmia;
providing an atrial defibrillation shock in response to the detected atrial arrhythmia;
providing pacing pulses at a first delay after an atrial defibrillation shock, wherein the pacing pulses have a pacing rate at an initial value that is well above an intrinsic rate, and wherein the pacing pulses have a pacing rate at an initial value that is in a range of 100 to 200 pacing pulses per minute;
decreasing the pacing rate from the initial value, wherein decreasing the pacing rate includes increasing an interval between the pacing pulses by a set value in the range of 7.5 to 10 milliseconds in a repeated manner until at least one intrinsic atrial contraction is detected;

determining the intrinsic atrial rate using the at least one intrinsic atrial contraction; and increasing the pacing rate above the determined intrinsic atrial rate.

11. A method, comprising:

sensing an atrial cardiac signal;

analyzing the atrial cardiac signal to detect an atrial tachyarrhythmia;

providing an atrial defibrillation shock in response to the detected atrial arrhythmia;

providing pacing pulses at a first delay after an atrial defibrillation shock, wherein the pacing pulses have a pacing rate at an initial value that is well above an intrinsic rate, and wherein the pacing pulses have a pacing rate at an initial value that is in a range of 100 to 200 pacing pulses per minute;

decreasing the pacing rate from the initial value, wherein decreasing the pacing rate includes increasing an interval between the pacing pulses by a set value in the range of 7.5 to 10 milliseconds in a repeated manner until at least one intrinsic atrial contraction is detected;

determining the intrinsic atrial rate using the at least one intrinsic atrial contraction; and increasing the pacing rate to just above the determined intrinsic atrial rate.

* * * * *

UNITED STATES PATENT AND TRADEMARK OFFICE
CERTIFICATE OF CORRECTION

| | |
|---|---|
| PATENT NO. | : 7,421,294 B2 |
| APPLICATION NO. | : 10/975553 |
| DATED | : September 2, 2008 |
| INVENTOR(S) | : Chen et al. |

Page 1 of 1

It is certified that error appears in the above-identified patent and that said Letters Patent is hereby corrected as shown below:

On the title page, item (73), in "Assignee", in column 1, line 2, delete "MO (US)" and insert -- MN (US) --, therefor.

Signed and Sealed this

Third Day of February, 2009

JOHN DOLL
*Acting Director of the United States Patent and Trademark Office*